United States Patent
Hattori et al.

(10) Patent No.: US 9,448,207 B2
(45) Date of Patent: Sep. 20, 2016

(54) QUALITY EVALUATION APPARATUS, QUALITY EVALUATION METHOD, AND EVALUATION SUBSTRATE

(71) Applicant: Murata Manufacturing Co., Ltd., Nagaokakyo-shi, Kyoto-fu (JP)

(72) Inventors: Kazuo Hattori, Nagaokakyo (JP); Isamu Fujimoto, Nagaokakyo (JP); Tadateru Yamada, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 222 days.

(21) Appl. No.: 13/966,445

(22) Filed: Aug. 14, 2013

(65) Prior Publication Data
US 2014/0060192 A1    Mar. 6, 2014

(30) Foreign Application Priority Data
Aug. 29, 2012   (JP) ................................ 2012-188773

(51) Int. Cl.
*G01N 29/04*   (2006.01)
*G01N 29/14*   (2006.01)

(52) U.S. Cl.
CPC ............. *G01N 29/04* (2013.01); *G01N 29/14* (2013.01)

(58) Field of Classification Search
CPC ................................................. G01R 31/1209
USPC ............ 361/301.1, 308.1; 73/571, 584, 587; 324/658
See application file for complete search history.

(56) References Cited

U.S. PATENT DOCUMENTS

| 2001/0004941 | A1* | 6/2001 | Inoue | H05K 1/165 174/260 |
|---|---|---|---|---|
| 2004/0066589 | A1* | 4/2004 | Togashi | H01G 2/065 361/15 |
| 2004/0183147 | A1* | 9/2004 | Togashi | H01G 2/065 257/414 |
| 2008/0174935 | A1* | 7/2008 | Togashi | H01G 4/012 361/306.3 |
| 2010/0123995 | A1* | 5/2010 | Otsuka | H01G 2/06 361/308.1 |
| 2011/0114378 | A1* | 5/2011 | Yoshii | H01G 2/065 174/260 |

FOREIGN PATENT DOCUMENTS

| JP | 08-055752 A | 2/1996 | |
|---|---|---|---|
| JP | 2004-134430 A | 4/2004 | |
| JP | 2005-195396 A | 7/2005 | |
| JP | 2005195396 A * | 7/2005 | ............... G01H 3/10 |
| JP | 2010-123614 A | 6/2010 | |
| JP | 2012-094784 A | 5/2012 | |
| JP | 2012-99538 A | 5/2012 | |

OTHER PUBLICATIONS

Official Communication issued in corresponding Japanese Patent Application No. 2012-188773, mailed on Aug. 5, 2014.

* cited by examiner

*Primary Examiner* — Michael A Lyons
*Assistant Examiner* — Suman K Nath
(74) *Attorney, Agent, or Firm* — Keating & Bennett, LLP (57) ABSTRACT

In a quality evaluation method, an evaluation substrate that includes a mounting region, in which a multilayer capacitor is to be mounted, in a center portion of the evaluation substrate is fixed in place using a plurality of fixed portions at corner portions of the evaluation substrate, each of which is a same distance from the mounting region. A voltage is applied to the multilayer capacitor mounted on the mounting region of the evaluation substrate. Sound is collected using a microphone that is near the multilayer capacitor mounted on the evaluation substrate.

16 Claims, 8 Drawing Sheets

QUALITY EVALUATION APPARATUS, QUALITY EVALUATION METHOD, AND EVALUATION SUBSTRATE

BACKGROUND OF THE INVENTION

1. Field of the Invention

The present invention relates to a quality evaluation apparatus, a quality evaluation method, and an evaluation substrate that evaluates the quality of a multilayer capacitor.

2. Description of the Related Art

Chip components, particularly monolithic ceramic capacitors have been widely used in mobile terminals such as cellular phones and various electronic apparatuses such as personal computers. A monolithic ceramic capacitor includes a substantially rectangular component body including inner electrodes and dielectric ceramics that are alternately stacked on top of one another and outer electrodes formed on opposing end portions of the component body.

A monolithic ceramic capacitor is electrically and physically connected to a circuit board of an electronic apparatus by directly placing the outer electrodes onto mounting lands of the circuit board and bonding each of the mounting lands and the corresponding outer electrode using a bonding agent such as solder.

When an alternating-current voltage or a direct-current voltage on which an alternating current component is superimposed is applied to such a monolithic ceramic capacitor, mechanical deformation vibration is generated due to the piezoelectric and electrostrictive effects of a dielectric ceramic. The vibration of the monolithic ceramic capacitor is transferred to the circuit board, and the circuit board vibrates. When the circuit board vibrates, vibration sound audible to the human ear may sometimes be generated.

In order to solve the above problem, various configurations have been considered. For example, Japanese Unexamined Patent Application Publication No. 8-55752 describes a method of mounting a monolithic ceramic capacitor onto a substrate such that surfaces of inner electrodes are perpendicular to a surface of the substrate. Japanese Unexamined Patent Application Publication No. 2012-94784 describes that end surfaces of outer electrodes of a monolithic ceramic capacitor are clamped between connection terminals, and that the monolithic ceramic capacitor is mounted on a circuit board via the outer electrodes. Japanese Unexamined Patent Application Publication No. 2004-134430 describes that a monolithic ceramic capacitor is indirectly mounted on a circuit board via an interposer that is made of an insulating board.

Although various means for suppressing occurrences of vibration sound such as those described in Japanese Unexamined Patent Application Publication No. 8-55752, Japanese Unexamined Patent Application Publication No. 2012-94784, and Japanese Unexamined Patent Application Publication No. 2004-134430, which have been described above, have been proposed, there is no method of precisely measuring vibration sound and no method of comparing vibration sounds. Vibration sound changes depending on the frequency of a voltage that is applied to a multilayer capacitor. For example, in a method of measuring vibration sound that is disclosed in Japanese Unexamined Patent Application Publication No. 2012-94784, changes in vibration sound due to variation in frequency are complicated. In addition, the vibration sound changes in a more complicated manner depending on variations in a mounting state of a multilayer capacitor. When such complicated changes in vibration sound occur, it becomes difficult to compare vibration sounds of various multilayer capacitors. Therefore, there is a need for a method of precisely measuring vibration sounds of a substrate on which a multilayer capacitor is mounted.

SUMMARY OF THE INVENTION

Accordingly, preferred embodiments of the present invention provide a quality evaluation apparatus, a quality evaluation method, and an evaluation substrate capable of easily evaluating the quality of a multilayer capacitor with which there are only negligible variations in measurement results.

According to a preferred embodiment of the present invention, a quality evaluation apparatus that evaluates quality of a multilayer capacitor includes a multilayer body including a stack of inner electrodes and dielectric layers and outer electrodes that are located on a surface of the multilayer body and each of which is electrically connected to a different one of the inner electrodes, the quality evaluation apparatus including a substrate on which the multilayer capacitor is to be mounted, a fixing unit that fixes the substrate in place, a unit that applies a voltage to the multilayer capacitor that is to be mounted on the substrate, and a sound collecting unit disposed near the multilayer capacitor, which is to be mounted on the substrate. The substrate preferably is a regular polygonal or substantially regular polygonal substrate that includes a mounting region, in which the multilayer capacitor is to be mounted, in a center portion or approximate center portion of the substrate and includes a plurality of fixed portions that are fixed in place by the fixing unit. The fixed portions are each located a same distance from the mounting region and are each a corner portion of the substrate.

In such a configuration, the distances from each of the sides of the substrate to the mounting region are equal to one another, and the distances from each of the fixed portions to the mounting region are also equal to one another. Therefore, a concentric circular or substantially concentric circular vibration mode is generated. As a result, measurement of vibration sound can be stably performed, evaluation of vibration sound can be easily performed, and variations in sound pressure level can be significantly reduced.

In the quality evaluation apparatus according to a preferred embodiment of the present invention, the substrate may have a square or substantially square shape.

In such a configuration, the substrate can be easily formed.

In the quality evaluation apparatus according to a preferred embodiment of the present invention, the fixed portions may be located on a surface of the substrate, and the fixing unit may fix the substrate in place by pressing the fixed portions in a thickness direction of the substrate.

In such a configuration, the substrate can be stably fixed in place.

In the quality evaluation apparatus according to a preferred embodiment of the present invention, the fixed portions may project from the surface of the substrate.

In such a configuration, displacement of a fixed position of the substrate can be significantly reduced, and variations in sound pressure level can be significantly reduced.

In the quality evaluation apparatus according to a preferred embodiment of the present invention, the fixed portions may be made of a metal.

In such a configuration, the fixed portions can be more strongly fixed, and variations in sound pressure level can be reduced.

In the quality evaluation apparatus according to a preferred embodiment of the present invention, each of the fixed portions may include a through hole extending through the substrate, and the fixing unit may include a joint component including a shaft portion to be inserted into the through hole and a head portion having a diameter larger than a diameter of the through hole and may include a support portion into which the shaft portion of the joint component is to be fitted.

In such a configuration, the substrate can be easily fixed in place.

According to another preferred embodiment of the present invention, a quality evaluation apparatus that evaluates quality of a multilayer capacitor includes a multilayer body including a stack of inner electrodes and dielectric layers, and outer electrodes that are located on a surface of the multilayer body and each of which is electrically connected to a different one of the inner electrodes, the quality evaluation apparatus including a substrate on which the multilayer capacitor is to be mounted, a fixing unit that fixes the substrate in place, a unit that applies a voltage to the multilayer capacitor that is to be mounted on the substrate, and a sound collecting unit disposed in the vicinity of the multilayer capacitor, which is to be mounted on the substrate. The substrate is a circular or substantially circular substrate that includes a mounting region, in which the multilayer capacitor is to be mounted, in a center portion or approximate center portion of the substrate and includes a fixed portion that is fixed in place by the fixing unit, and the fixed portion preferably has a circular or substantially circular shape disposed around the mounting region of the substrate.

In such a configuration, the distance from the mounting region to the edge of the substrate is equal in all directions, and thus, a concentric circular vibration mode is generated. As a result, measurement of vibration sound can be stably performed, evaluation of vibration sound can be easily performed, and variations in sound pressure level can be significantly reduced.

In the quality evaluation apparatus according to a preferred embodiment of the present invention, the fixed portion may be located on a side surface of the substrate, and the fixing unit may fix the substrate in place by pressing the fixed portion in a direction toward a center of the substrate.

In such a configuration, the substrate can be easily fixed in place.

In the quality evaluation apparatus according to a preferred embodiment of the present invention, the fixed portion may be located on a surface of the substrate and arranged a ring shape or substantially ring shape, and the fixing unit may fix the substrate in place by pressing the fixed portion in a thickness direction of the substrate.

In such a configuration, the influence of variations in the external shape of the substrate caused by a processing operation can be reduced, and variations in sound pressure level can be significantly reduced.

In the quality evaluation apparatus according to a preferred embodiment of the present invention, the fixed portion may include a projecting portion projecting in a direction normal to the surface of the substrate, and the fixing unit may fix the substrate in place by pressing the projecting portion in the thickness direction of the substrate.

In such a configuration, displacement of a fixed position of the substrate can be significantly reduced, and variations in sound pressure level can be significantly reduced.

In the quality evaluation apparatus according to a preferred embodiment of the present invention, the fixed portion may be made of a metal.

In such a configuration, the fixed portions can be more strongly fixed, and variations in sound pressure level can be significantly reduced.

According to various preferred embodiments of the present invention, measurement of vibration sound can be stably performed, evaluation of vibration sound can be easily performed, and variations in sound pressure level can be significantly reduced by generating a concentric circular or substantially concentric circular vibration mode in a substrate. As a result, reliable results of quality evaluation can be obtained.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1A:
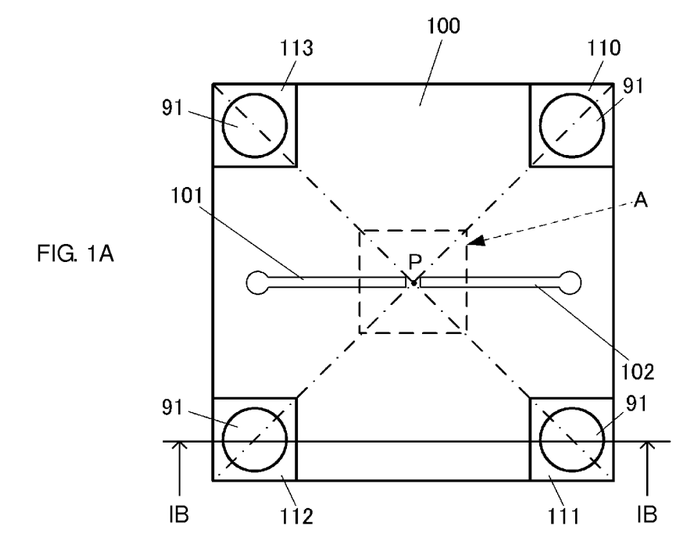
FIG. 1A is a plan view of a circuit board that is used for quality evaluation of a multilayer capacitor.
Figure 1B:
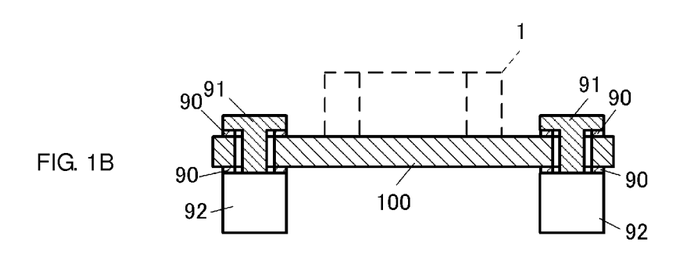
FIG. 1B is a sectional view taken along line I-I of FIG. 1A.
Figure 2:
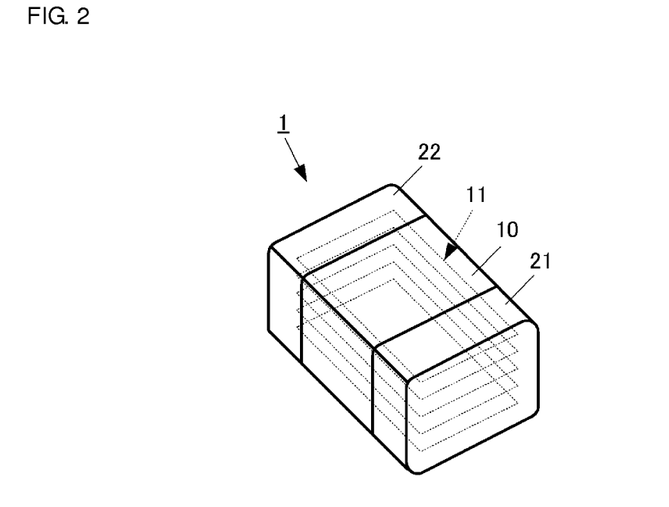
FIG. 2 is an external perspective view of a multilayer capacitor that is to be subjected to quality evaluation.

FIG. 1A is a plan view of a circuit board that is used for quality evaluation of a multilayer capacitor. FIG. 1B is a sectional view taken along line I-I of FIG. 1A. FIG. 2 is an external perspective view of a multilayer capacitor that is to be subjected to quality evaluation.

First, a multilayer capacitor 1 that is to be subjected to quality evaluation will be described. The multilayer capacitor 1 includes a ceramic multilayer body 10 preferably having a rectangular or substantially rectangular parallelepiped shape that is longer in one direction, for example. The multilayer body 10 includes a plurality of inner electrodes 11 each of which is tabular and preferably has a rectangular or substantially rectangular shape, for example. In the multilayer body 10, the inner electrodes 11 and ceramic layers (dielectric layers) are stacked in an alternating manner. The inner electrodes 11 include inner electrodes that are exposed from one end portion of the multilayer body 10 in a longitudinal direction and inner electrodes that are exposed at the other end portion of the multilayer body 10 in the longitudinal direction, and the inner electrodes are stacked in an alternating manner. The inner electrodes 11 are made of, for example, nickel.

Outer electrodes 21 and 22 are located on surfaces of the end portions of the multilayer body 10 that oppose each other in the longitudinal direction of the multilayer body 10. The outer electrodes 21 and 22 are connected to the corresponding inner electrodes 11 each of which is exposed from a surface of the multilayer body 10. The outer electrodes 21 and 22 are provided on the end surfaces of the multilayer body 10 in the longitudinal direction, and in addition, are arranged so as to extend from the end surfaces of the multilayer body 10 in the longitudinal direction onto the side surfaces of the multilayer body 10 in a width direction, the top surface of the multilayer body 10, and the bottom surface of the multilayer body 10.

Although, in the present preferred embodiment, the multilayer capacitor 1 in which the outer electrodes 21 and 22 are preferably located on the surfaces of the end portions of the multilayer body 10, which are opposite to each other in the longitudinal direction, has been described, the multilayer capacitor 1 is not limited to the above-described multilayer capacitor. The multilayer capacitor 1 may be a multilayer capacitor that includes three or more outer electrodes, for example. In addition, the multilayer capacitor 1 may be accompanied by a connection terminal, an interposer, or the like. Furthermore, the multilayer capacitor 1 may be an electronic component that is a combination of two or more multilayer capacitors. The multilayer capacitor 1 preferably has dimensions (length×width) of, for example, about 3.2 mm×about 1.6 mm, about 2.0 mm×about 1.25 mm, about 1.6 mm×about 0.8 mm, about 1.0 mm×about 0.5 mm, about 0.6 mm×about 0.3 mm, or the like.

An evaluation substrate 100 on which the multilayer capacitor 1 is to be mounted is used for quality evaluation of the multilayer capacitor 1. The evaluation substrate 100 preferably is made of an insulating resin and has a square or substantially square shape, for example. A mounting region A in which the multilayer capacitor 1 is to be mounted is located in a center portion of the evaluation substrate 100. More specifically, in the case where an intersection point of two diagonal lines (one dot chain lines in FIG. 1A) of the evaluation substrate 100 having a square or substantially square shape is an intersection point P (hereinafter referred to as a midpoint P), the mounting region A is arranged such that substantially the centers of the top surface and the bottom surface of the multilayer capacitor 1 that is to be mounted are superposed with the midpoint P.

Although, in FIG. 1A, the mounting region A is represented by a square dashed line for convenience of description, the mounting region A need not be disposed so as to be clearly divided from the other regions as long as the center or substantially the center of the multilayer capacitor 1, which is to be mounted, is superposed with the midpoint P.

Mounting electrode patterns 101 and 102 are located on the evaluation substrate 100. The mounting electrode patterns 101 and 102 are arranged so as to extend in opposite directions with the midpoint P interposed therebetween and to have a belt-like shape. The mounting electrode patterns 101 and 102 are electrically connected to the outer electrodes 21 and 22 of the multilayer capacitor 1, which is to be mounted in the mounting region A, respectively. The outer end portion of each of the mounting electrode patterns 101 and 102 is larger (has a larger width) than the other portions of the mounting electrode patterns 101 and 102 to allow application of a voltage. A voltage that has been applied to the outer end portions is applied to the outer electrodes 21 and 22 of the multilayer capacitor 1, which is mounted, via the mounting electrode patterns 101 and 102.

When an alternating-current voltage or a direct-current voltage on which an alternating current component is superimposed is applied to the outer electrodes 21 and 22, mechanical deformation vibration is generated in the multilayer capacitor 1 due to the piezoelectric and electrostrictive effects of a dielectric ceramic. The vibration is transferred to the evaluation substrate 100, and the evaluation substrate 100 vibrates.

Fixed portions 110, 111, 112, and 113 are provided at corner portions of the evaluation substrate 100. Each of the fixed portions 110, 111, 112, and 113 has a square or substantially square shape. A through hole is formed in the center of each of the fixed portions 110, 111, 112, and 113. A ring-shaped or substantially ring-shaped metallic portion 90 is provided along the circumferential edge of each of the through holes. The metallic portions 90 allow the circumferential edge portions of the through holes to project from the evaluation substrate 100. In other words, each of the metallic portions 90 corresponds to a projecting portion according to the present preferred embodiment of the present invention. Note that each of the metallic portions 90 is preferably defined by a wiring pattern, for example.

The evaluation substrate 100 is fixed in place by pressing the fixed portions 110, 111, 112, and 113 preferably using bolts 91 and supporting bars 92, for example, each of which corresponds to a fixing unit according to a preferred embodiment of the present invention in a thickness direction of the evaluation substrate 100. Each of the bolts 91 includes a shaft portion having a diameter smaller than an inner diameter of corresponding one of the metallic portions 90 and a head portion having a diameter larger than an inner diameter of a corresponding one of the metallic portions 90. Each of the shaft portions is inserted into the corresponding metallic portion 90 and screwed into the corresponding supporting bar 92, and the evaluation substrate 100 is clamped between the head portions of the bolts 91 and the supporting bars 92, so that the evaluation substrate 100 is fixed in place. Since the fixed portions 110, 111, 112, and 113 are arranged so as to be at the same distance from the midpoint P, variations in vibration of the evaluation substrate 100 are significantly reduced or prevented.

Even if the evaluation substrate 100 is strongly fixed in place, using the metallic portions 90 each of which has rigidity enables the evaluation substrate 100 to be more strongly fixed in place without the occurrence of breakage or the like as compared with the case of not using the metallic portions 90. Since each of the metallic portions 90 projects from the evaluation substrate 100, pressure is dispersed, and thus, the fixed state of the evaluation substrate 100 is not likely to change even if a position at which pressure is applied is displaced. Therefore, displacement of a fixed position of the evaluation substrate 100 is not likely to occur, and as a result, reliable measurement results can be obtained.

It is preferable that the bolts 91 and the supporting bars 92 that fix the evaluation substrate 100 in place be made of stainless steel or the like, for example, in order not to lose the vibration of the evaluation substrate 100. A ring washer may be used as each of the metallic portions 90. Alternatively, a projecting portion that is made of a resin or the like may be provided on the surface of the evaluation substrate 100 instead of providing each of the metallic portions 90.

Regarding the evaluation substrate 100 configured as described above, a vibration mode of the evaluation substrate 100 and sound pressure levels of the evaluation substrate 100 will be described below.

Figure 3A:
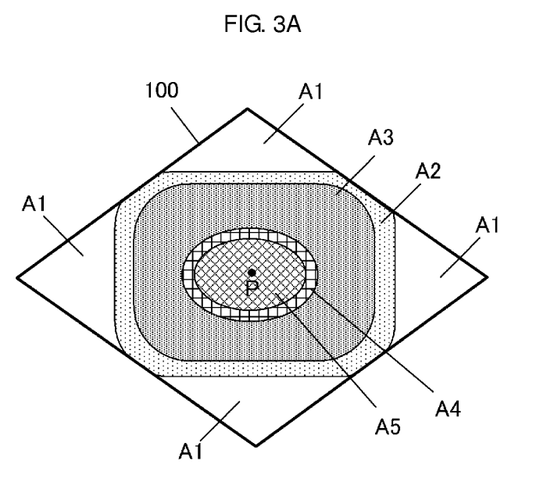
FIG. 3A is a diagram illustrating vibration displacement generated in an evaluation substrate.
Figure 3B:
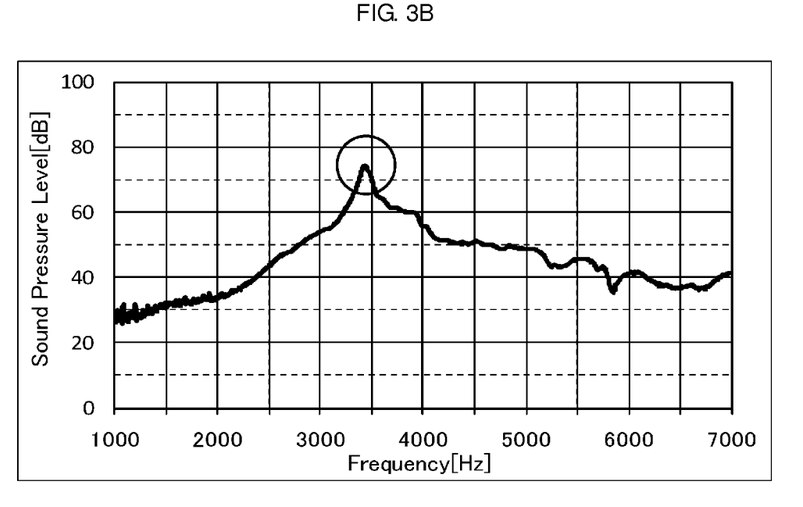
FIG. 3B is a diagram illustrating a relationship between vibration frequency and sound pressure level.

FIG. 3A is a diagram illustrating vibration displacement generated in the evaluation substrate 100. FIG. 3B is a diagram illustrating a relationship between vibration frequency and sound pressure level. Note that, in FIG. 3B, the evaluation substrate 100 that includes a mounting surface whose dimensions are preferably about 40 mm×about 40 mm, for example, is used. In FIG. 3B, the horizontal axis represents frequency (Hz), and the vertical axis represents sound pressure level (dB).

The evaluation substrate 100 preferably has a square or substantially square shape, and the distances from the midpoint P of the evaluation substrate 100 to each of the sides of the evaluation substrate 100 are the same as one another. Therefore, when the evaluation substrate 100 vibrates, the vibration modes in areas between the midpoint P and each of the sides become the same as one another. In addition, when the evaluation substrate 100 vibrates, the corner portions of the evaluation substrate 100, which are fixed in place, serve as vibration fixed ends. Thus, the amplitude of vibration becomes maximum at the midpoint P and becomes minimum at each of the corner portions. Therefore, the amplitude of vibration of the evaluation substrate 100 decreases with increasing distance from the midpoint P, and in FIG. 3A, the vibration displacement has a magnitude relationship of A1<A2<A3<A4<A5.

In the evaluation substrate 100 having a square or substantially square shape, the distances from each of the sides to the center of the evaluation substrate 100 are equal to one another, and the distances from each of the fixed portions 110, 111, 112, and 113 to the center of the evaluation substrate 100 are also equal to one another. Therefore, a circular or substantially concentric circular vibration mode is generated in the evaluation substrate 100. In the substantially concentric circular vibration mode, the evaluation substrate 100 resonates at substantially the same timing even if energy of a vibration source has a directional property, and thus, energy in all directions affects the resonance of the evaluation substrate 100. Therefore, regardless of the directional property of the vibration source, vibration sound can be evaluated using a single index, that is, the sound pressure level in the circular or substantially concentric circular vibration mode.

In the case where the evaluation substrate 100 having a square or substantially square shape is used, when the vibration frequency is about 3.5 kHz, the vibration sound of the evaluation substrate 100 has a maximum value of about 75 dB as indicated by the circle in FIG. 3B. In this way, measurement results can be obtained using a single index.

In contrast, in the case where a rectangular or substantially rectangular evaluation substrate having long sides and short sides is used, the distance from one of the long sides of the substrate to the center of the substrate and the distance from one of the short sides of the substrate to the center of the substrate are different from each other, and thus, various vibration modes are present in the substrate. In the case where energy of a vibration source has a directional property, the amplitude of the vibration in a vibration mode mainly determined by a long side dimension and the amplitude of the vibration in a vibration mode mainly determined by a short side dimension may sometimes be affected by the directional property of the energy of the vibration source. Therefore, a change in a mounting direction of a component or the like affects the vibration sound, and the way in which the vibration sound is affected differs depending on the vibration mode. As a result, the evaluation of the vibration sound becomes complicated. The case where the rectangular or substantially rectangular evaluation substrate is used will be described below for the purpose of comparison with the present preferred embodiment.

Figure 4A:
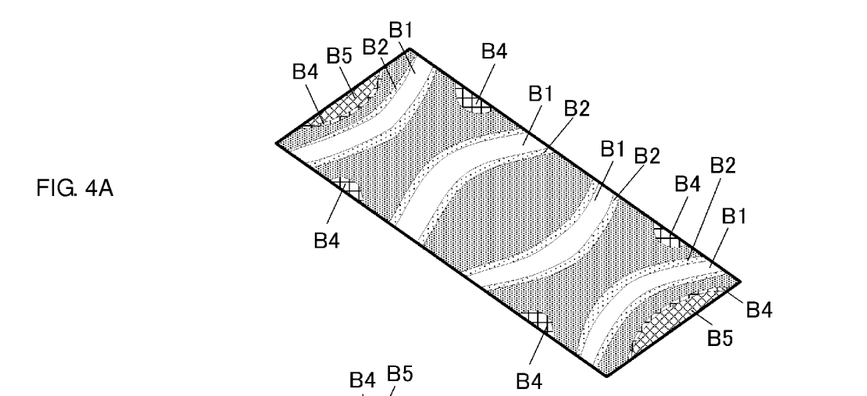
FIGS. 4A and 4B are diagrams illustrating vibration displacement generated in a rectangular or substantially rectangular evaluation substrate.
Figure 4B:
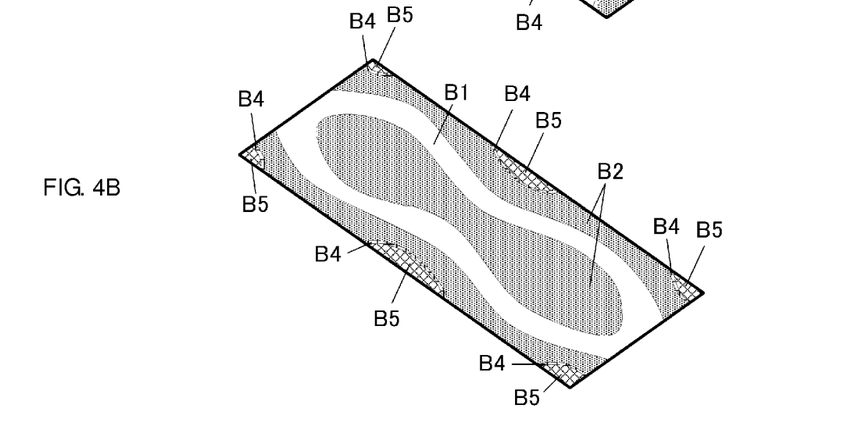
Figure 4C:
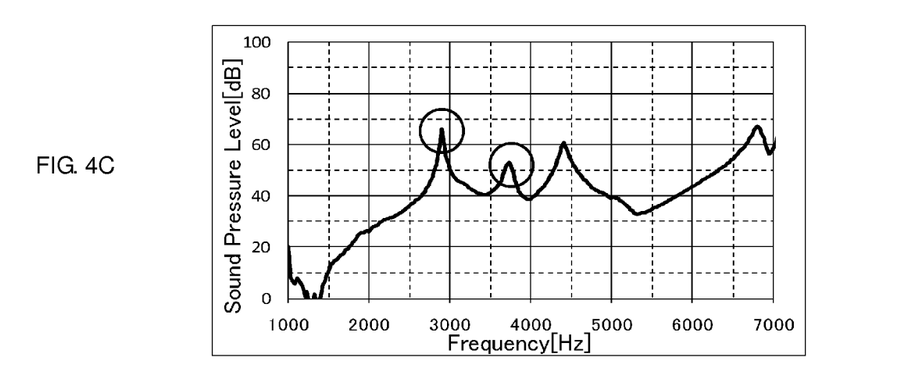
FIG. 4C is a diagram illustrating a relationship between vibration frequency and sound pressure level.

FIGS. 4A and 4B are diagrams illustrating vibration displacement generated in the rectangular or substantially rectangular evaluation substrate. FIG. 4C is a diagram illustrating a relationship between vibration frequency and sound pressure level.

The evaluation substrate illustrated in FIGS. 4A and 4B includes a mounting surface whose dimensions are about 100 mm×about 40 mm. A multilayer capacitor is mounted on the substantially central portion of the evaluation substrate. The evaluation substrate is fixed at four positions each two of which is about 35 mm away from the center of one of the sides of the evaluation substrate in the longitudinal direction. In the evaluation substrate, the distance from the center portion at which the amount of vibration displacement is the largest to one of the long sides and the distance from the center portion to one of the short sides are different from each other, and thus, different vibration modes are generated in the evaluation substrate.

Regions B1, B2, B3, B4, and B5 are illustrated in the evaluation substrate of FIGS. 4A and 4B. The regions are numbered in ascending order of the amount of the vibration displacement. When the vibration frequency is about 2.9 kHz, the vibration sound has a maximum value of about 68 dB, and the vibration mode illustrated in FIG. 4A is generated. When the vibration frequency is about 3.8 kHz, the vibration sound has a maximum value of about 55 dB, and the vibration mode illustrated in FIG. 4B is generated. Thus, in contrast to the evaluation substrate 100 having a square or substantially square shape, in the rectangular or substantially rectangular evaluation substrate, a change in a mounting direction of a component or the like affects the vibration sound, and the way in which the vibration sound is affected differs depending on the vibration mode. Therefore, the evaluation of the vibration sound becomes complicated, and as a result, reliable measurement results cannot be obtained.

Figure 5:
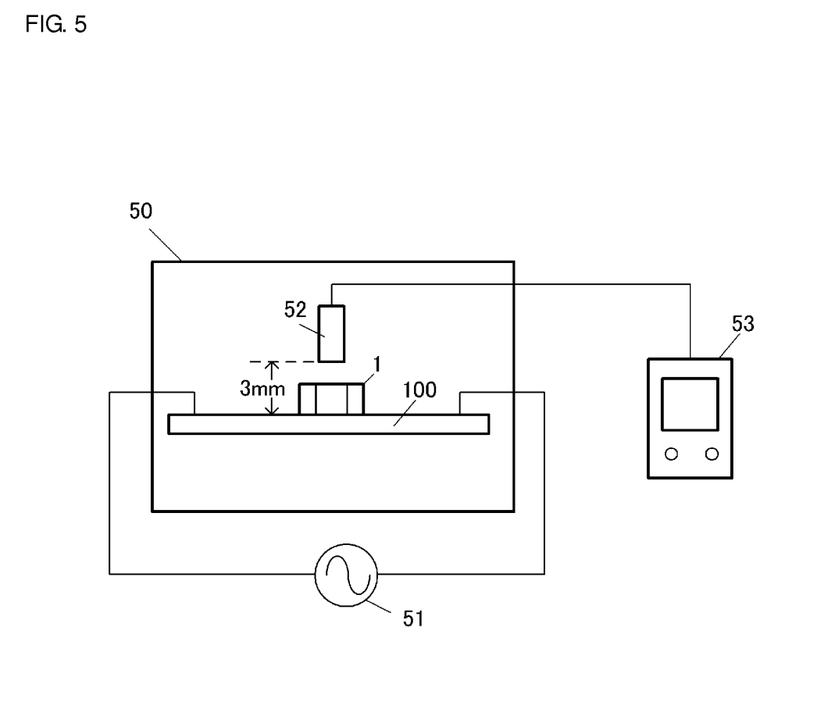
FIG. 5 is a schematic diagram of a quality evaluation apparatus.

FIG. 5 is a schematic diagram of a quality evaluation apparatus. As illustrated in FIG. 5, measurement of the vibration sound of the evaluation substrate 100 is performed by storing the evaluation substrate 100 on which the multilayer capacitor 1 is mounted in a non-echo box 50. The quality evaluation apparatus includes a power supply apparatus 51 that applies a voltage to the mounting electrode patterns 101 and 102, which are located on the evaluation substrate 100.

In addition, the quality evaluation apparatus includes a microphone 52. The microphone 52 is disposed directly above the multilayer capacitor 1, which is mounted on the evaluation substrate 100, and collects the vibration sound of the evaluation substrate 100. As illustrated in FIG. 3A, the amount of the vibration displacement is the largest at a region A5 in the vicinity of the midpoint P, and thus, a position at which the microphone 52 is disposed may be in the vicinity of the region A5. The microphone 52 is preferably disposed about 3 mm away from the evaluation substrate 100, for example. The microphone 52 is connected to a fast Fourier transform (FFT) analyzer 53 that detects a sound pressure level.

Figure 6A:
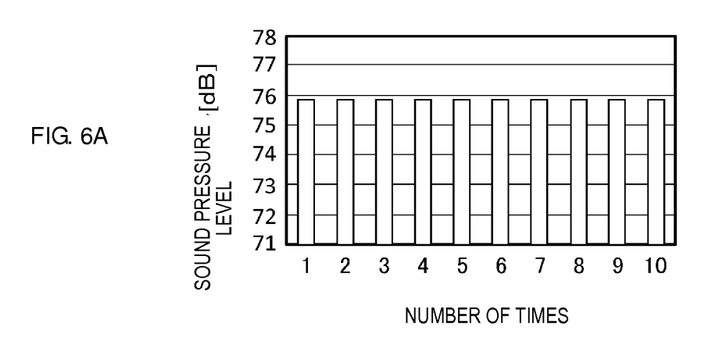
FIG. 6A illustrates experimental results obtained by measuring several times the sound pressure level of an evaluation substrate according to a preferred embodiment of the present invention.
Figure 6B:
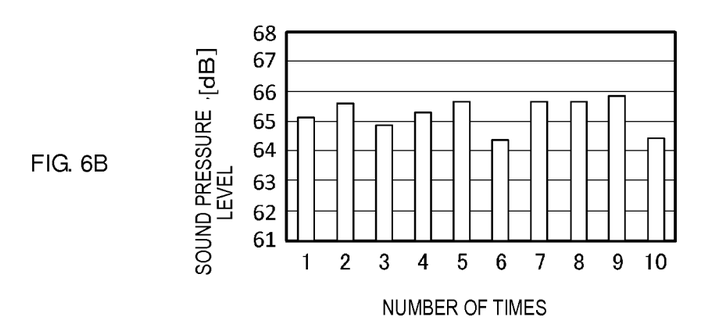
FIG. 6B illustrates experimental results obtained by measuring several times the sound pressure level of the rectangular or substantially rectangular evaluation substrate.

FIG. 6A illustrates experimental results obtained by measuring several times the sound pressure level of the evaluation substrate 100 according to the present preferred embodiment. FIG. 6B illustrates experimental results obtained by measuring several times the sound pressure level of the substantially rectangular evaluation substrate.

As illustrated in FIG. 6A, in the case where the evaluation substrate 100 according to the present preferred embodiment is used, a measurement result that is a sound pressure level of about 76 dB is obtained from all ten measurements. In other words, a variation in measurement results is small. In contrast, as illustrated in FIG. 6B, in the case where the rectangular or substantially rectangular evaluation substrate is used, there is variation in measurement results. Accordingly, reliable measurement results can be obtained by performing quality evaluation using the evaluation substrate 100 according to the present preferred embodiment.

Although the evaluation substrate 100 preferably has a square or substantially square shape in the above-described preferred embodiment, the evaluation substrate 100 is not limited to such a shape. The evaluation substrate 100 may have a circular or substantially circular shape or a regular polygonal or substantially regular polygonal shape. In other words, the evaluation substrate 100 may have any shape as long as the distances from the center portion of the evaluation substrate 100 in which the amount of vibration displacement is large to each of end portions of the evaluation substrate 100 are the same as one another.

Figure 8A:
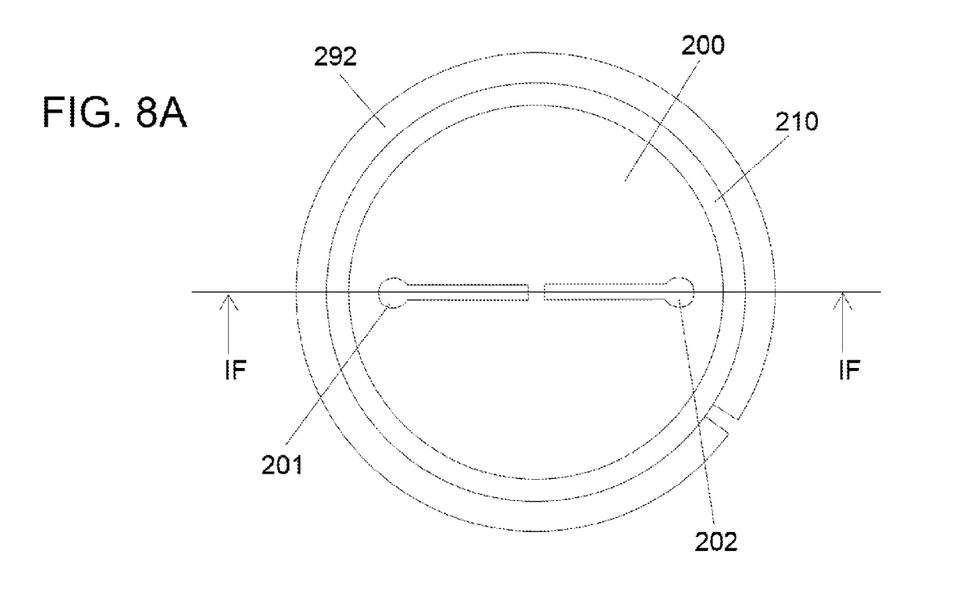
FIG. 8A is a plan view of a circular or substantially circular substrate that is used for quality evaluation of the multilayer capacitor.
Figure 8B:
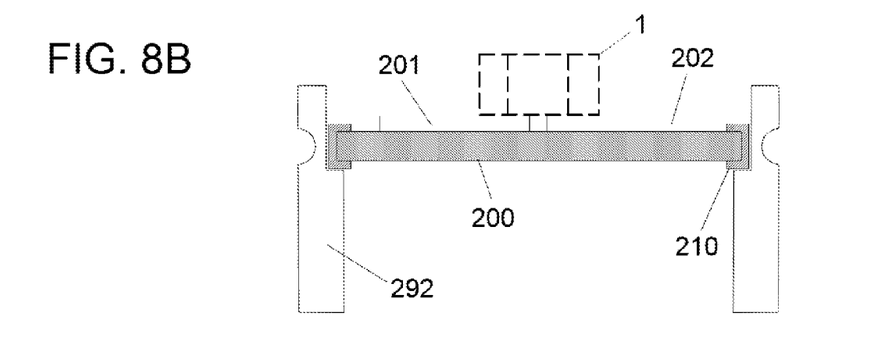
FIG. 8B is a sectional view taken along line IF-IF of FIG. 8A.

FIGS. 8A and 8B illustrate a circular or substantially circular substrate 200 that is used for quality evaluation of the multilayer capacitor 1. The substrate 200 is a circular or substantially circular substrate that includes a mounting region, in which the multilayer capacitor 1 is to be mounted in a center portion or approximate center portion of the substrate 200, and includes a fixed portion 210 that is fixed in place by a fixing unit 292. The fixed portion 210 preferably has a circular or substantially circular shape disposed around the mounting region of the substrate 200. Mounting electrode patterns 201 and 202 are located on the evaluation substrate 200.

Figure 7A:
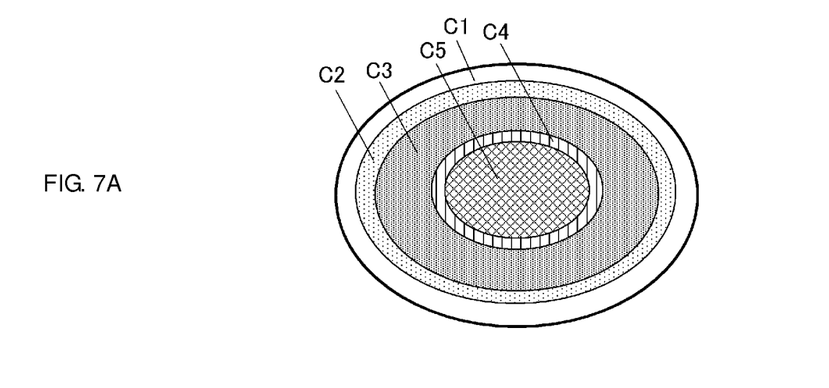
FIG. 7A is a diagram illustrating vibration displacement generated in a circular or substantially circular evaluation substrate.
Figure 7B:
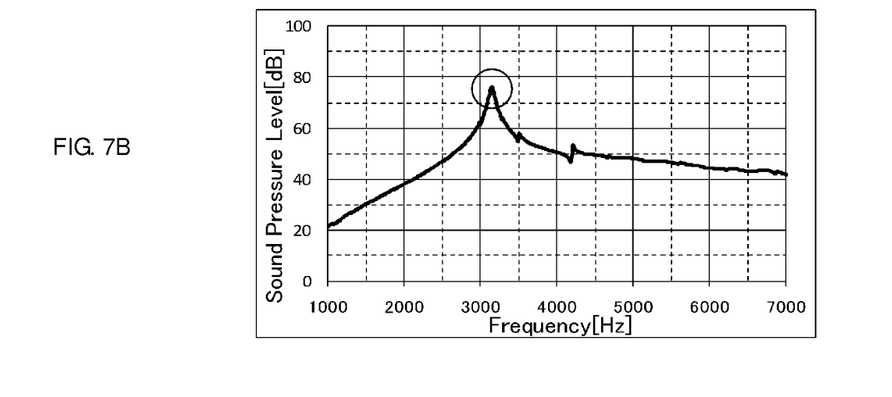
FIG. 7B is a diagram illustrating a relationship between vibration frequency and sound pressure level.

FIG. 7A is a diagram illustrating vibration displacement generated in a circular or substantially circular evaluation substrate, such as the substrate 200 as shown in FIGS. 8A and 8B. FIG. 7B is a diagram illustrating a relationship between vibration frequency and sound pressure level. Note that an evaluation substrate that includes a mounting surface having a diameter of about 40 mm, for example, is preferably used in FIG. 7B. As shown 8A and 8B, the entire outer periphery of the circular or substantially circular evaluation substrate 200 is fixed in place with, for example, a fixed portion 210 and a fixing unit 292 that is made of a resin in which a groove or a hole in which the evaluation substrate 200 can be accommodated is formed. In addition, the circular or substantially circular evaluation substrate 200 is fixed in place by being applied with pressure exerted from the outer periphery of the evaluation substrate 200 toward the center or approximate center of the evaluation substrate 200. Note that the substantially circular evaluation substrate 200 may be fixed in place by being pressed in a thickness direction of the evaluation substrate as described above in regards to FIG. 1B.

In the case where the evaluation substrate 200 has a circular or substantially circular shape, as illustrated in FIG. 7A, the distance from the center of the evaluation substrate 200 to the edge of the evaluation substrate 200 is equal in all directions, and thus, a concentric circular vibration mode is generated. When the evaluation substrate 200 vibrates, the outer periphery of the evaluation substrate 200 that is fixed in place serves as a vibration fixed end. Thus, the amplitude of vibration becomes maximum at the midpoint of the evaluation substrate 200 and becomes minimum at the outer periphery of the evaluation substrate 200. Therefore, the vibration of the evaluation substrate 200 decreases with increasing distance from the midpoint, and in FIG. 7A, the vibration displacement has a magnitude relationship of $C1 < C2 < C3 < C4 < C5$.

As indicated by the circle in FIG. 7B, when the vibration frequency is about 2.6 kHz, the vibration sound of the evaluation substrate has a value of about 75 dB. Thus, in the case where a circular or substantially circular evaluation substrate is used, measurement results can be obtained using a single index. Therefore, when vibration sound of the evaluation substrate is measured, reliable measurement results can be obtained.

In the concentric circular vibration mode, the amplitude of vibration is further less likely to be affected by the directional property of energy of a vibration source compared with in a vibration mode generated in a regular polygonal or substantially regular polygonal evaluation substrate. Therefore, evaluation of vibration sound can be stably performed even if there is a very small displacement of a mounting direction of a component.

In the case where a method of reducing vibration sound that is to be evaluated is to perform a processing operation on a substrate or to perform a fixing operation on a substrate, the evaluation substrate according to the present preferred embodiment of the present invention having the above-described configuration undergoes a processing operation or a fixing operation that is performed as a method of reducing the vibration sound.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A quality evaluation apparatus that evaluates quality of a multilayer capacitor that includes a multilayer body including inner electrodes and dielectric layers and outer electrodes located on a surface of the multilayer body and each of which is electrically connected to a different one of the inner electrodes, the quality evaluation apparatus comprising:

a substrate on which the multilayer capacitor is to be mounted;

a fixing unit that fixes the substrate in place;

a unit that applies a voltage to the multilayer capacitor that is to be mounted on the substrate; and a sound collecting unit disposed near the multilayer capacitor to be mounted on the substrate; wherein the substrate is a regular polygonal or substantially regular polygonal substrate that includes a mounting region in which the multilayer capacitor is to be mounted in a center portion or approximate center portion of the substrate and includes a plurality of fixed portions that are fixed in place by the fixing unit;

the plurality of fixed portions are each located on a surface of the substrate a same distance from the mounting region and are each provided at a respective corner portion of the surface of the substrate; and the plurality of fixed portions project from the surface of the substrate.

2. The quality evaluation apparatus according to claim 1, wherein the substrate has a square or substantially square shape.

3. The quality evaluation apparatus according to claim 1, wherein the fixing unit fixes the substrate in place by pressing the plurality of fixed portions in a thickness direction of the substrate.

4. The quality evaluation apparatus according to claim 3, wherein the plurality of fixed portions are made of a metal.

5. The quality evaluation apparatus according to claim 3, wherein each of the plurality of fixed portions includes a through hole extending through the substrate; and the fixing unit includes a joint component including a shaft portion to be inserted into the through hole and a head portion having a diameter larger than a diameter of the through hole and includes a support portion into which the shaft portion of the joint component is to be fitted.

6. A quality evaluation apparatus that evaluates quality of a multilayer capacitor that includes a multilayer body including inner electrodes and dielectric layers and outer electrodes located on a surface of the multilayer body and each of which is electrically connected to a different one of the inner electrodes, the quality evaluation apparatus comprising:

a substrate on which the multilayer capacitor is to be mounted;

a fixing unit that fixes the substrate in place;

a unit that applies a voltage to the multilayer capacitor to be mounted on the substrate; and a sound collecting unit disposed near the multilayer capacitor to be mounted on the substrate; wherein the substrate is a circular or substantially circular substrate that includes a mounting region in which the multilayer capacitor is to be mounted in a center portion or substantially center portion of the substrate and includes a fixed portion that is fixed in place by the fixing unit;

the fixed portion has a circular or a substantially circular shape disposed around the mounting region of the substrate;

the fixed portion is located on a side surface of the substrate;

the fixing unit fixes the substrate in place by pressing the fixed portion in a direction toward a center of the substrate; and the fixing unit is made of a resin and includes a groove or a hole in which the substrate can be accommodated.

7. The quality evaluation apparatus according to claim 6, wherein the fixed portion includes a projecting portion projecting in a direction normal to the surface of the substrate; and the fixing unit fixes the substrate in place by pressing the projecting portion in the thickness direction of the substrate.

8. The quality evaluation apparatus according to claim 6, wherein the fixed portion is made of a metal.

9. A quality evaluation method of evaluating quality of a multilayer capacitor that includes a multilayer body including inner electrodes and dielectric layers and outer electrodes that are located on a surface of the multilayer body and each of which is electrically connected to a different one of the inner electrodes, the quality evaluation method comprising:

mounting the multilayer capacitor in a mounting region that is located in a center portion or approximate center portion of a regular polygonal or substantially regular polygonal substrate;

fixing the substrate using a plurality of fixed portions that are disposed on a surface of the substrate at positions that are a same distance from the mounting region of the substrate and that are each provided at a corner portion of the substrate, and using a fixing unit;

applying a voltage to the multilayer capacitor to be mounted on the substrate; and collecting sound using a sound collecting unit that is disposed near the multilayer capacitor to be mounted on the substrate; wherein the plurality of fixed portions project from the surface of the substrate.

10. The quality evaluation method according to claim 9, wherein the substrate has a square or substantially square shape.

11. The quality evaluation method according to claim 9, wherein the plurality of fixed portions are located on a surface of the substrate; and the substrate is fixed in place by pressing the plurality of fixed portions using the fixing unit in a thickness direction of the substrate.

12. The quality evaluation method according to claim 11, wherein each of the plurality of fixed portions includes a through hole that is formed in the substrate;

a projecting portion is formed along an opening of the through hole;

the fixing unit includes a joint component including a shaft portion to be inserted into the through hole and a head portion having a diameter larger than a diameter of the through hole and includes a support portion into which the shaft portion of the joint component is to be fitted; and the substrate is fixed in place by fitting the shaft portion, which has been inserted into the through hole, into the support portion and pressing the projection portion using the head portion and the support portion in the thickness direction of the substrate.

13. A quality evaluation method of evaluating quality of a multilayer capacitor that includes a multilayer body including inner electrodes and dielectric layers and outer electrodes that are located on a surface of the multilayer body and each of which is electrically connected to a different one of the inner electrodes, the quality evaluation method comprising:

mounting the multilayer capacitor on a mounting region that is located in a center portion or approximate center portion of a circular or substantially circular substrate;

fixing the substrate in place using a fixed portion that has a circular or substantially circular shape disposed around the mounting region of the substrate and a fixing unit;

applying a voltage to the multilayer capacitor that is to be mounted on the substrate; and collecting sound using a sound collecting unit that is disposed near the multilayer capacitor to be mounted on the substrate; wherein the fixed portion is located on a side surface of the substrate;

the fixing unit fixes the substrate in place by pressing the fixed portion in a direction toward a center of the substrate; and the fixing unit is made of a resin and includes a groove or a hole in which the substrate can be accommodated.

14. An evaluation substrate used for quality evaluation of a multilayer capacitor that is mounted, the evaluation substrate comprising:

a regular polygonal or substantially regular polygonal base that includes a mounting surface in a center portion or approximate center portion in which a mounting region where the multilayer capacitor is to be mounted is provided; and a fixed portion that is provided on a surface of the base and located in each of a plurality of corner portions of the base; wherein the fixed portion is a metallic portion or a projecting portion that is located on the mounting surface of the base; and the fixed portion projects from the mounting surface of the substrate.

15. The evaluation substrate according to claim 14, wherein the base has a square or substantially square shape.

16. The evaluation substrate according to claim 14, wherein the fixed portion includes a through hole provided in the base.

* * * * *